(12) United States Patent
Cho et al.

(10) Patent No.: US 9,157,840 B2
(45) Date of Patent: Oct. 13, 2015

(54) MULTIPLE SEPARATION DEVICE AND METHOD OF SEPARATING BLOOD CANCER CELL

(71) Applicant: Electronics and Telecommunications Research Institute, Daejeon (KR)

(72) Inventors: Seong-Mok Cho, Daejeon (KR); Dae-Sik Lee, Daejeon (KR); Jeong Won Park, Daejeon (KR); Moon Youn Jung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 149 days.

(21) Appl. No.: 13/787,725

(22) Filed: Mar. 6, 2013

(65) Prior Publication Data
US 2013/0236885 A1 Sep. 12, 2013

(30) Foreign Application Priority Data

Mar. 9, 2012 (KR) .......................... 10-2012-0024678
Oct. 18, 2012 (KR) .......................... 10-2012-0116207

(51) Int. Cl.
| | | |
|---|---|---|
| C12N 5/00 | (2006.01) | |
| A01N 1/02 | (2006.01) | |
| G01N 1/34 | (2006.01) | |
| G01N 33/543 | (2006.01) | |
| G01N 33/574 | (2006.01) | |
| C12N 5/07 | (2010.01) | |
| G01N 33/49 | (2006.01) | |

(52) U.S. Cl.
CPC ............ *G01N 1/34* (2013.01); *G01N 33/54326* (2013.01); *G01N 33/54386* (2013.01); *G01N 33/57488* (2013.01)

(58) Field of Classification Search
None
See application file for complete search history.

(56) References Cited

U.S. PATENT DOCUMENTS

2011/0020459 A1 * 1/2011 Achrol et al. ................. 424/520

* cited by examiner

*Primary Examiner* — James Martinell

(57) ABSTRACT

The present inventive concept provides a multiple separation device and a method of separating a blood cancer cell using the same. In the device and the method, a blood sample is put in a fine channel and then cancer cells can be separated according to the type of cancer by controlling a flow velocity of the blood or a magnetic force of ferromagnetic pattern.

8 Claims, 11 Drawing Sheets

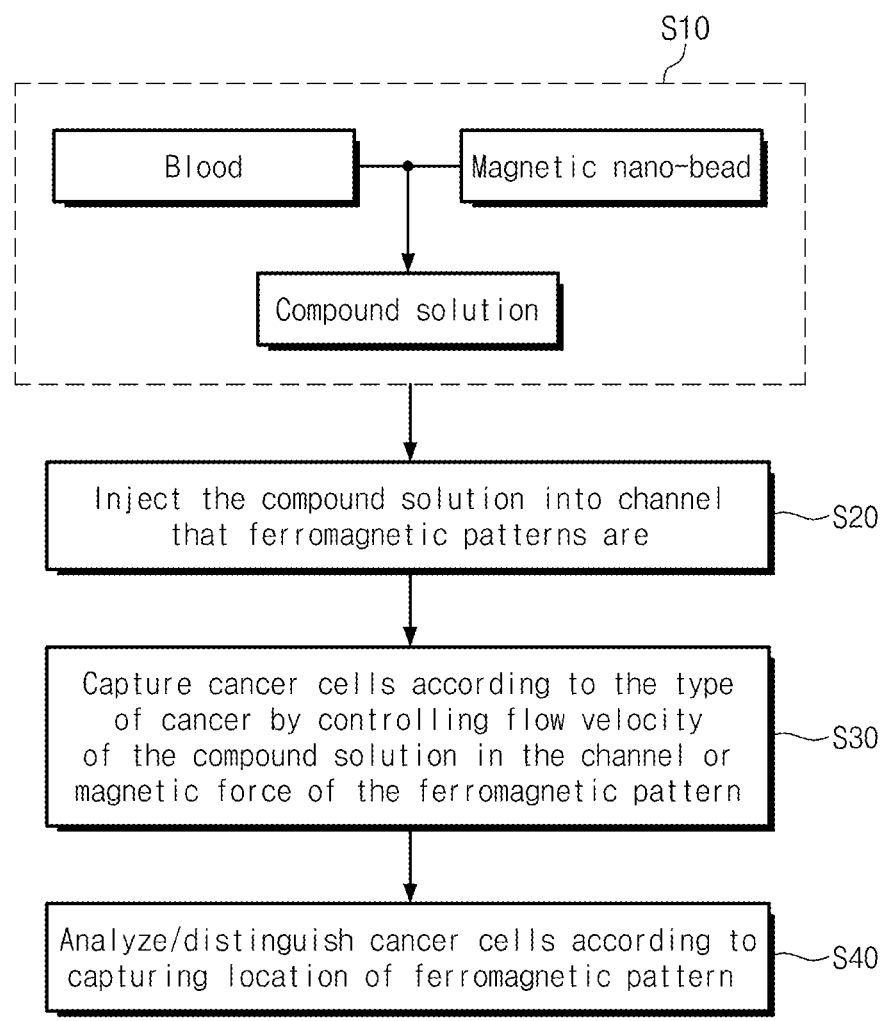

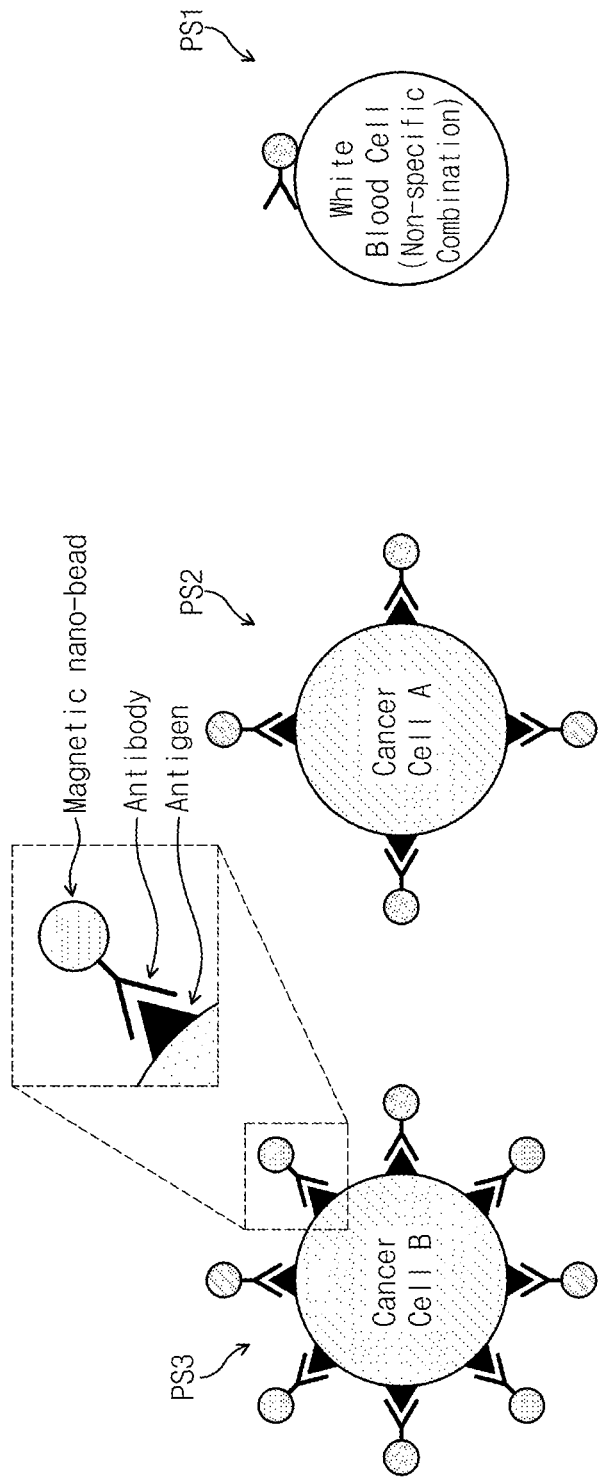

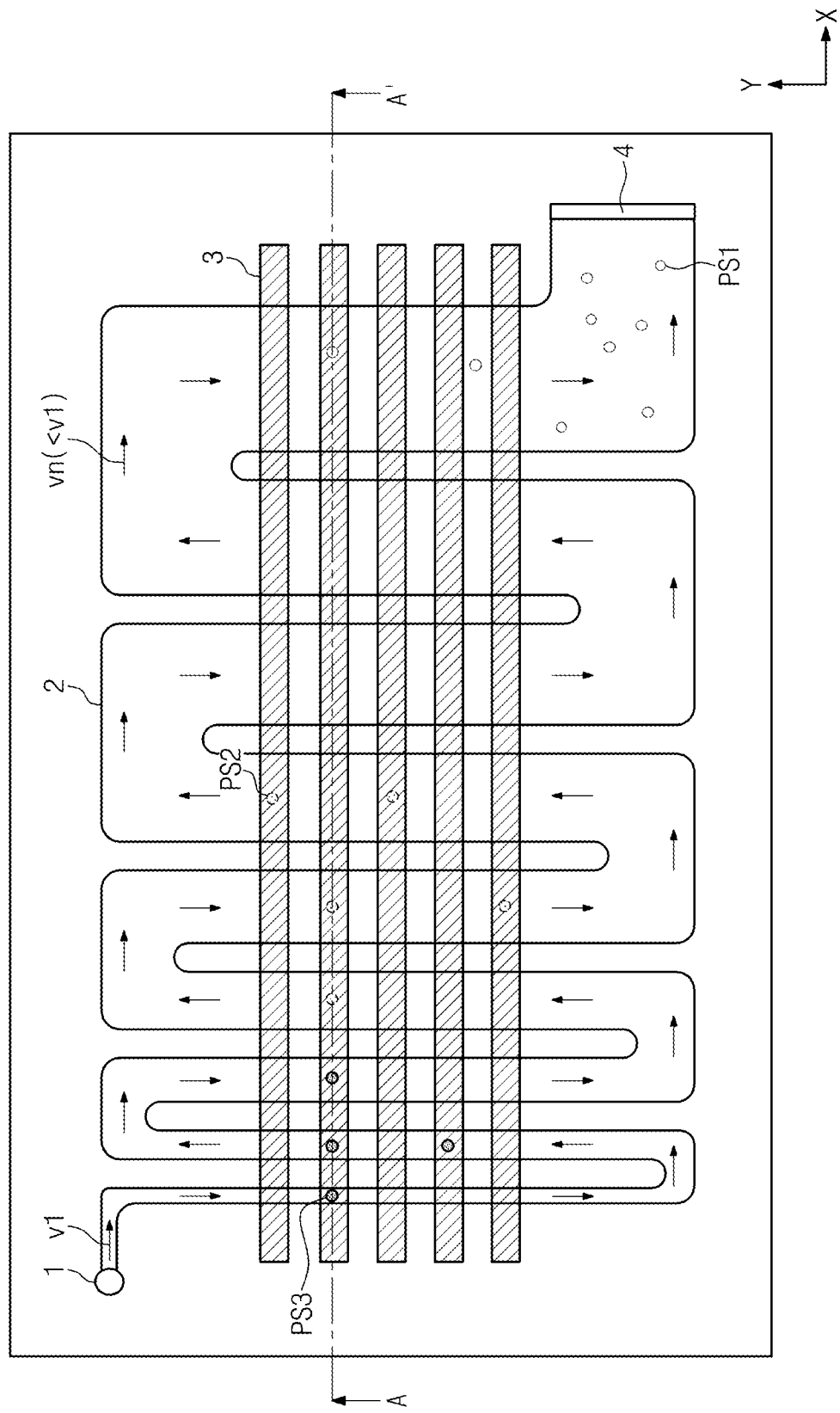

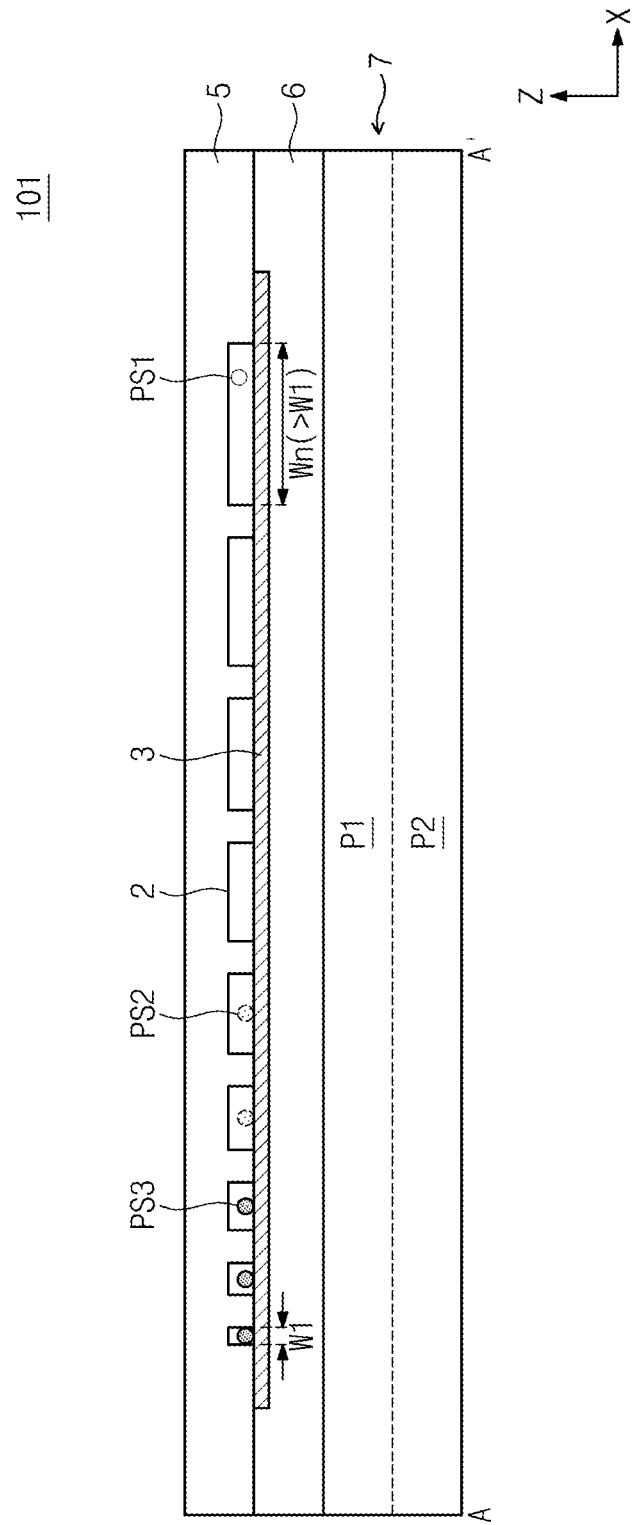

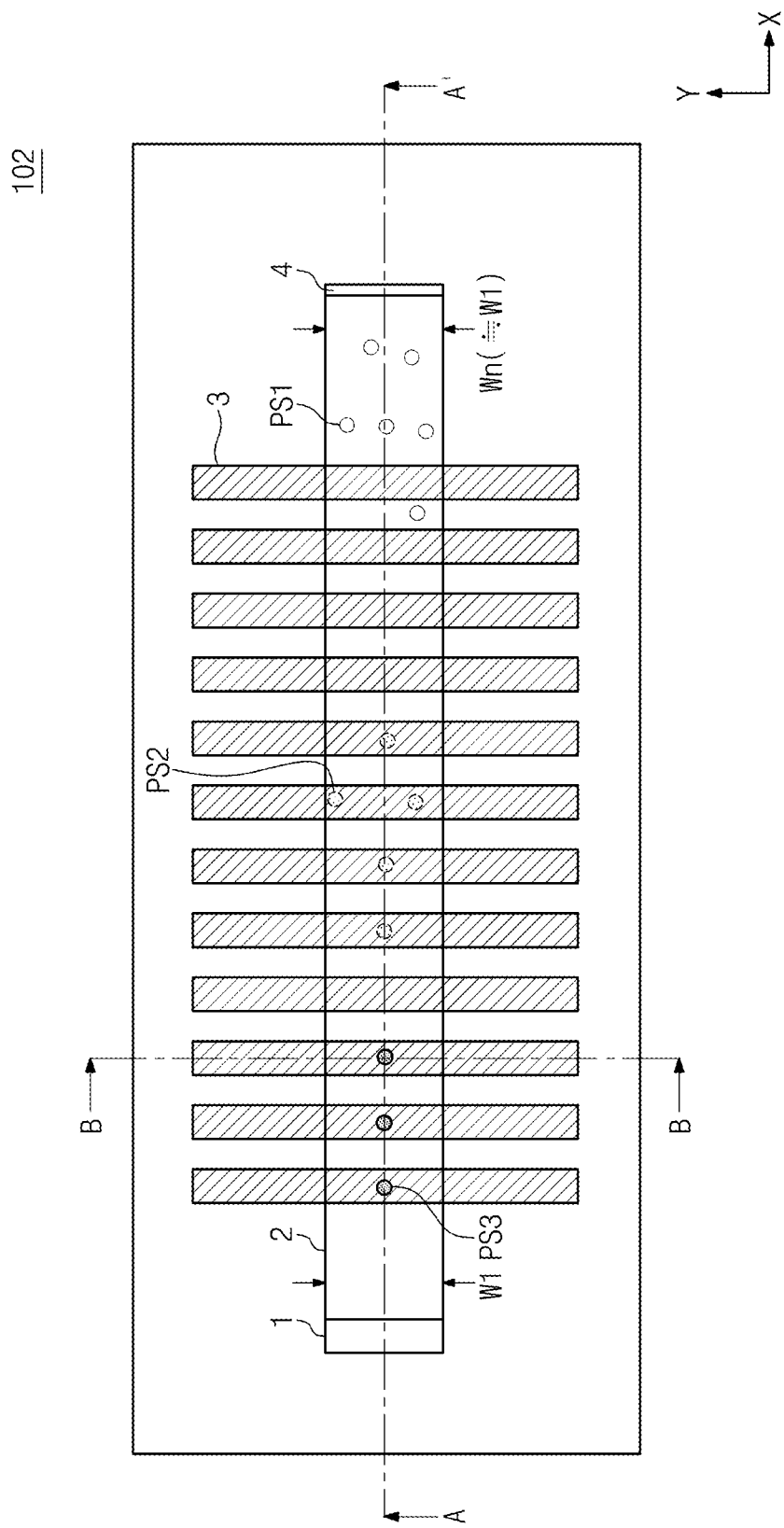

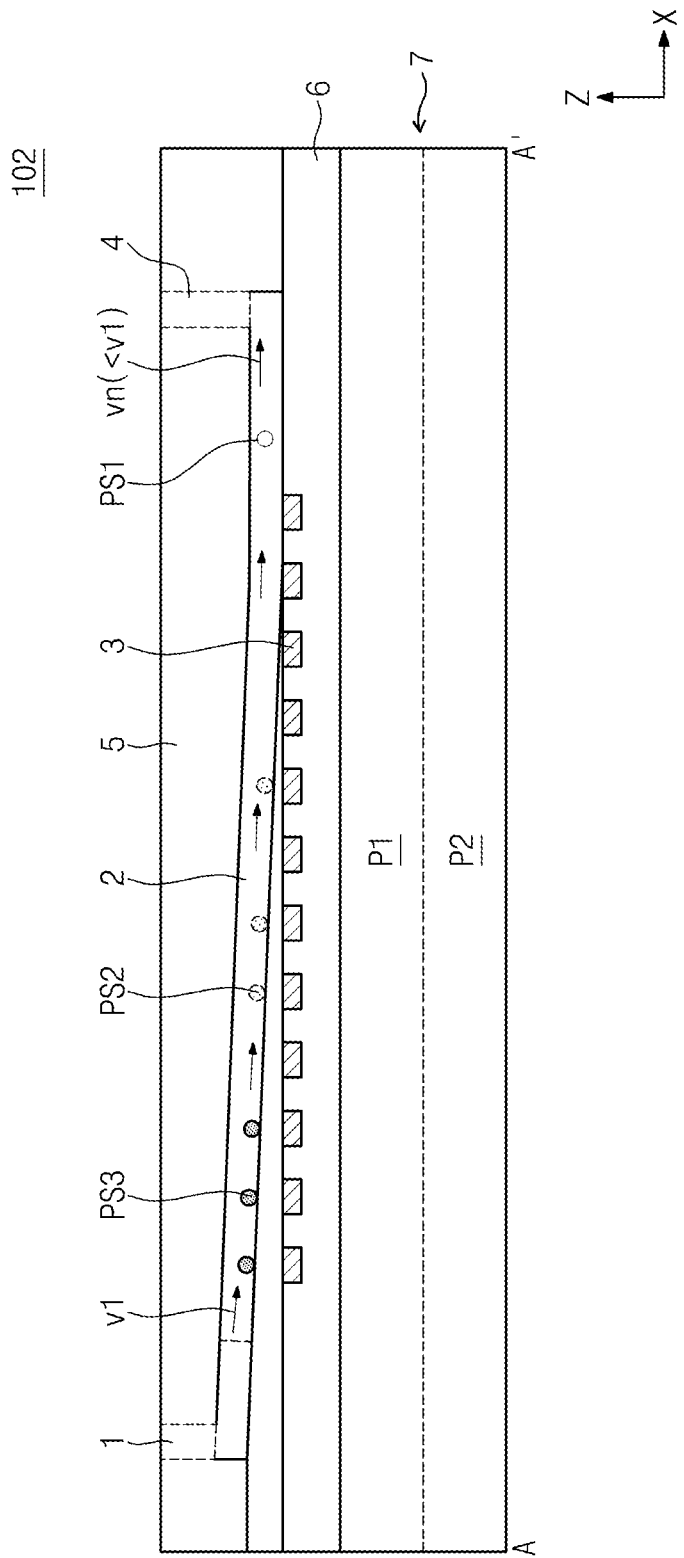

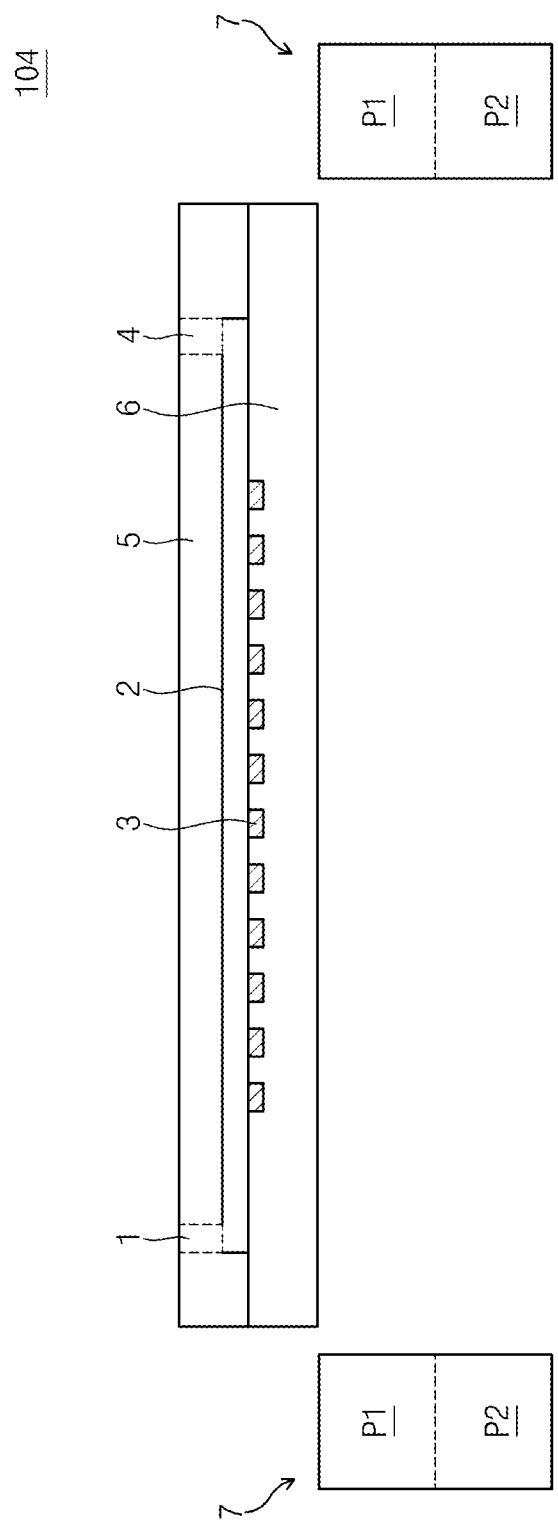

MULTIPLE SEPARATION DEVICE AND METHOD OF SEPARATING BLOOD CANCER CELL

CROSS-REFERENCE TO RELATED APPLICATIONS

This U.S. non-provisional patent application claims priority under 35 U.S.C. §119 of Korean Patent Application No. 10-2012-0024678, filed on Mar. 9, 2012 and No. 10-2012-0116207, filed on Oct. 18, 2012, the entire contents of which are hereby incorporated by reference.

BACKGROUND

The present inventive concept herein relates to multiple separation devices of material species including a biomaterial and methods of separating blood cancer cells.

As a preparation tool for diagnosis and treatment in the field of medicine, and an ultimate object or a different analysis in the field of study, a cell type or a separation of components in a cell is required. The blood cancer cell indicates a cancer cell exists in a peripheral blood of a cancer patient and also indicates cancer cells which are left out of primary lesion or metastasis lesion. The blood cancer cell is expected as a strong biomarker in a cancer diagnosis, a treatment prognosis analysis, a minute metastasis analysis, etc. Since a blood cancer cell analysis has an advantage of non-invasive method as compared with an existing cancer diagnosis method, it has bright prospects as a future cancer diagnosis method. However, since a blood cancer cell has a very low blood distribution ratio, that is, one cancer cell per one billion cells or one cancer cell per white blood cells of $10^6$~$10^7$, it is very difficult to perform an accurate analysis and a very sophisticated analysis method is required.

Various methods as a blood cancer separation method are being studied. However, the methods have disadvantages that a long test time is required, information only on whether a cancer cell exists and the quantity of cancer cells is suggested, and it is difficult to analyze types of cancer. Interference by non-specifically combined blood cells becomes a problem.

SUMMARY

Embodiments of the inventive concept provide a multiple separation device. The multiple separation device may include a channel through which a compound solution flows; and a ferromagnetic pattern disposed under a bottom surface of the channel. A flow velocity of the compound solution or a magnetic force of the ferromagnetic pattern is changed depending on a location of the channel.

Embodiments of the inventive concept also provide a method of separating a blood cancer cell. The method may include producing a compound solution including cancer cells with which a magnetic nano-bead is combined by mixing a magnetic nano-bead with which antibody specifically reacting to a cancer cell is combined and a blood to be tested; injecting the compound solution into a channel that ferromagnetic patterns are disposed on a bottom surface of the channel; and capturing cancer cells depending on the type of the cancer cells by controlling a flow velocity of the compound solution in the channel or changing a magnetic force of the ferromagnetic pattern.

BRIEF DESCRIPTION OF THE FIGURES

Preferred embodiments of the inventive concept will be described below in more detail with reference to the accompanying drawings. The embodiments of the inventive concept may, however, be embodied in different forms and should not be constructed as limited to the embodiments set forth herein. Rather, these embodiments are provided so that this disclosure will be thorough and complete, and will fully convey the scope of the inventive concept to those skilled in the art. Like numbers refer to like elements throughout.

FIG. 1 is a flow chart illustrating a method of separating a blood cancer cell in accordance with some embodiments of the inventive concept.

FIG. 2 illustrates material species included in a compound solution in accordance with some embodiments of the inventive concept.

FIG. 5A is a top plan view illustrating a multiple separation device in accordance with second embodiment of the inventive concept.

FIG. 5B is a cross sectional view taken along the line A-A' of FIG. 5A.

FIG. 6A is a top plan view illustrating a multiple separation device in accordance with third embodiment of the inventive concept.

FIG. 6B is a cross sectional view taken along the line A-A' of FIG. 6A.

FIGS. 7 and 8 are cross sectional views of a multiple separation device in accordance with further embodiments of the inventive concept.

DETAILED DESCRIPTION OF THE EMBODIMENTS

Figure 3A:
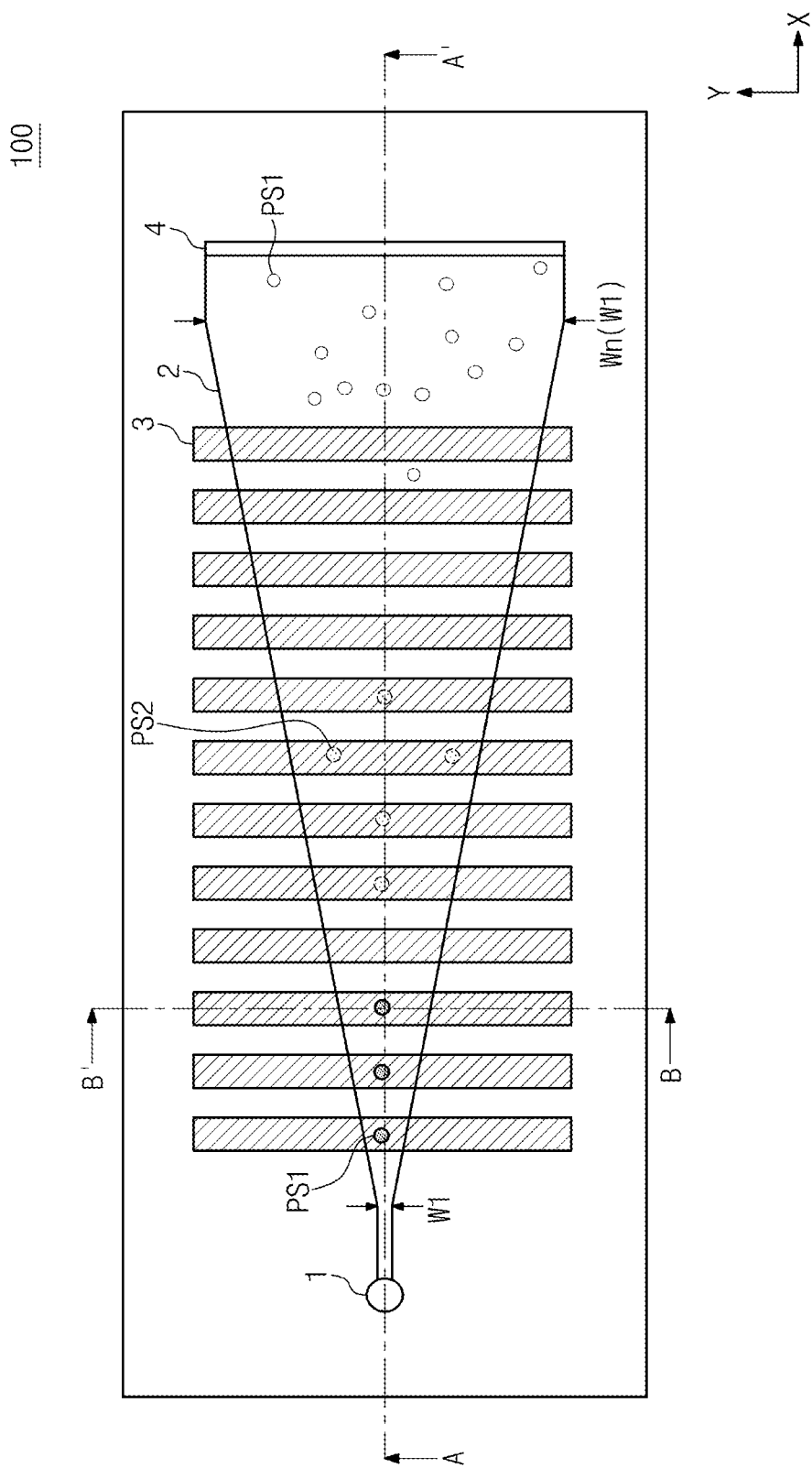
FIG. 3A is a top plan view illustrating a multiple separation device in accordance with first embodiment of the inventive concept.

Embodiments of inventive concepts will be described more fully hereinafter with reference to the accompanying drawings, in which embodiments of the invention are shown. This inventive concept may, however, be embodied in many different forms and should not be construed as limited to the embodiments set forth herein. Rather, these embodiments are provided so that this disclosure will be thorough and complete, and will fully convey the scope of the inventive concept to those skilled in the art. In the drawings, the size and relative sizes of layers and regions may be exaggerated for clarity. Like numbers refer to like elements throughout.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. As used herein, the term "and/or" includes any and all combinations of one or more of the associated listed items and may be abbreviated as "/".

It will also be understood that when an element such as a layer, region or substrate is referred to as being "on" or "onto" another element, it may lie directly on the other element or intervening elements or layers may also be present.

It will be understood that, although the terms first, second, etc. may be used herein to describe various elements, these elements should not be limited by these terms. These terms are only used to distinguish one element from another. For example, a first region/layer could be termed a second region/ layer, and, similarly, a second region/layer could be termed a first region/layer without departing from the teachings of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Figure 3B:
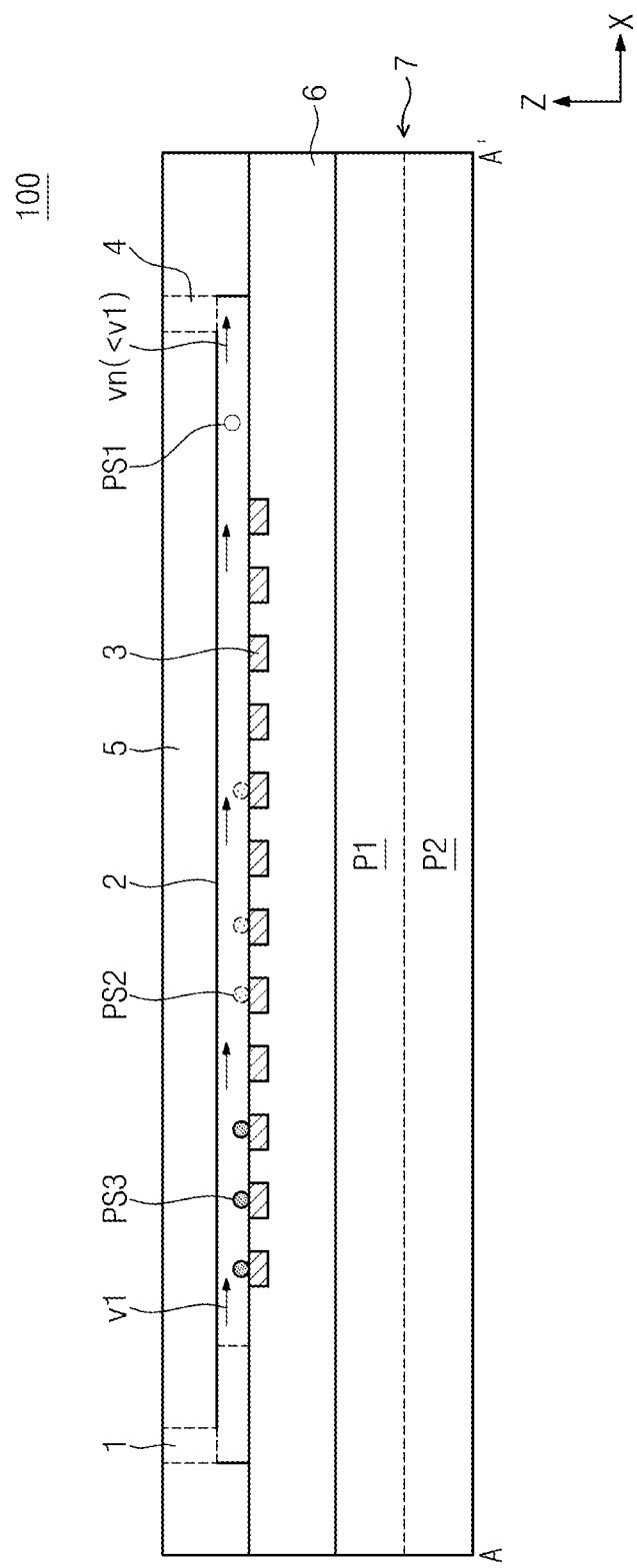
FIGS. 3B and 3C are cross sectional views taken along the lines A-A' and B-B' of FIG. 3A respectively.
Figure 3C:
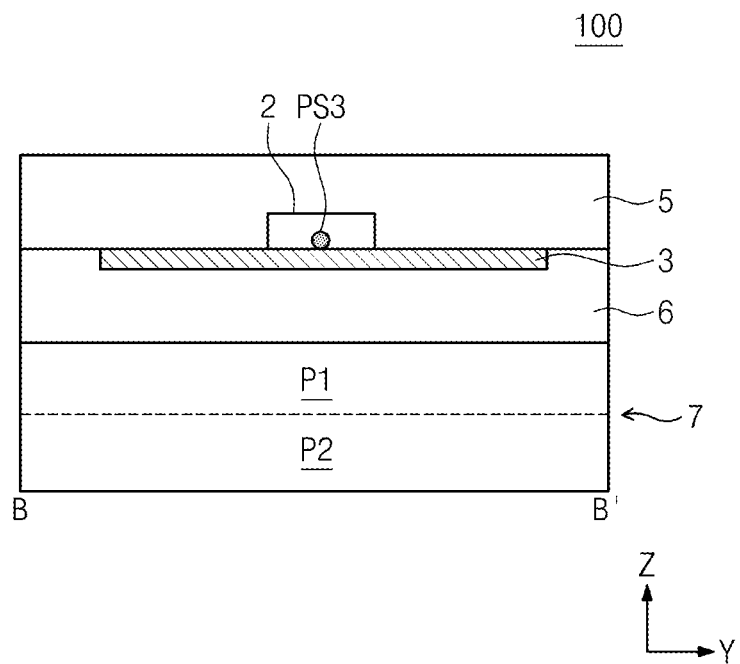

FIG. 1 is a flow chart illustrating a method of separating a blood cancer cell in accordance with some embodiments of the inventive concept. FIG. 2 illustrates material species included in a compound solution in accordance with some embodiments of the inventive concept. FIG. 3A is a top plan view illustrating a multiple separation device in accordance with first embodiment of the inventive concept. FIGS. 3B and 3C are cross sectional views taken along the lines A-A' and B-B' of FIG. 3A respectively.

Referring to FIGS. 1 and 2, in a method separating a blood cancer cell in accordance with some embodiments of the inventive concept, a magnetic nano-bead with which antibody specifically reacting to a cancer cell is combined and a blood to be tested are mixed to produce a compound solution (S10). The blood may include normal cells (first material species, PS2) such as a white blood cell, and a cancer cell A (second material species, PS1) and a cancer cell B (third material species, PS3) different from each other. In the case that the cancer cells PS2 and PS3 are different from each, the number of markers (e.g., antigen) manifested in a cancer cell is different. In case of EpCAM (epithelial cellular adhesion molecule) marker, there is a big difference in the number of markers manifested per one cancer cell depending on cancer type. That is, the number of EpCAM manifestations of breast cancer cell SKBr-3 per cell is about 500,000, the number of EpCAM manifestations of prostate cancer cell PC3-9 per cell is about 50,000, and the number of EpCAM manifestations of bladder cancer cell T-24 per cell is about 2,000. Thus, if antibody specifically reacting to EpCAM combines with a magnetic nano-bead and then the magnetic nano-bead is mixed with a blood of cancer patient, there is a big difference in the number of magnetic nano-beads which combine with a cancer cell depending on cancer type. The difference in the number of magnetic nano-beads being combined per cell may be used to separate a cancer using magnetic field. As the number of magnetic nano-beads increases, magnetization becomes great. As illustrated in FIG. 2, the magnetic nano-bead can specifically combine with a normal cell like a white blood cell but the number of magnetic nano-beads which combine with a white blood cell may be much smaller than the number of magnetic nano-beads which combine with markers of cancer cells. If the first material species PS1, the second material species PS2 and the third species PS3 have first magnetization, second magnetization and third magnetization respectively, the second magnetization is greater than the first magnetization and is smaller than the third magnetization.

The compound solution made by a blood including the magnetic nano-bead is separated using multiple separation devices of first through third embodiments.

First Embodiment

Referring to FIGS. 3A through 3C, a multiple separation device 100 includes an inlet 1 for the compound solution, an outlet 4 for the compound solution, and a channel 2 connecting the inlet 1 and the outlet 4. In the channel 2, the compound solution flows in a first direction X. The channel 2 may be provided by a substrate 6 providing the outlet 4 and a cover 5 providing the inlet 1 and a groove while covering the substrate 6. The substrate 6 and the cover 5 may be formed from a material such as glass or plastic that has low reactivity.

Ferromagnetic patterns 3 are disposed under a bottom surface of the channel 2. The ferromagnetic patterns 3 can be formed from any material having a ferromagnetic characteristic such as Ni, Co, Fe or compounds thereof. The ferromagnetic pattern 3 pulls magnetic particles in a fluid to disturb the flow of particles.

To magnetize the ferromagnetic pattern 3 and keep a constant magnetization state of the ferromagnetic pattern 3, a permanent magnet 7 may be disposed under the substrate 6. The permanent magnet 7 may include a first polar P1 and a second polar P2 which are opposite to each other. The first polar P1 may be, for example, an N-polar and the second polar P2 may be, for example, a S-polar. The ferromagnetic patterns 3 have an elongated bar shape in a second direction Y crossing the first direction X and are disposed to be spaced apart from each other at regular intervals. The ferromagnetic patterns 3 may have the same magnetic force.

The compound solution includes the first material species PS1 which is a normal cell, a second material species PS2 which is a cancer cell A and a third material species PS3 which is a cancer cell B. In the present embodiment, the types of the cancer cell are two but three or more types of the cancer are possible.

Referring to FIGS. 1 and 3A through 3C, the compound solution is injected into the inlet 1. The compound solution is injected into the channel 2 that the ferromagnetic patterns 3 having a specific magnetic force according to their locations are disposed on a bottom surface of the channel 2 (S20). In the channel 2, cancer cells are captured depending on the type of cancer cell by controlling a flow velocity of the compound solution or a magnetic force of the ferromagnetic pattern 3 (S30). In the first and second embodiments, a method of capturing cancer cells depending on the type of cancer cell by controlling a flow velocity of the compound solution is disclosed and in the third embodiment, a method of capturing cancer cells depending on the type of cancer cell by controlling a magnetic force of the ferromagnetic pattern 3 is disclosed.

Referring back to FIGS. 3A through 3C, a width (W1, Wn) of the channel 2 is widened as approaching the outlet 4 from the inlet 1. That is, a width (W1) of the channel 2 adjacent to the inlet 1 is smaller than a width (Wn) of the channel 2 adjacent to the outlet 4. A width (W1, Wn) of the channel 2 may be continuously widened as approaching the outlet 4 from the inlet 1. At all the locations, a bottom surface of the channel 2 may be flat and a thickness of the channel 2 may be uniform. A flow velocity (v1, vn) of the compound solution in the channel 2 becomes slow as approaching the outlet 4 from the inlet 1. That is, the flow velocity v1 of the compound solution adjacent to the inlet 1 is faster than the flow velocity vn of the compound solution adjacent to the outlet 4.

Figure 4:
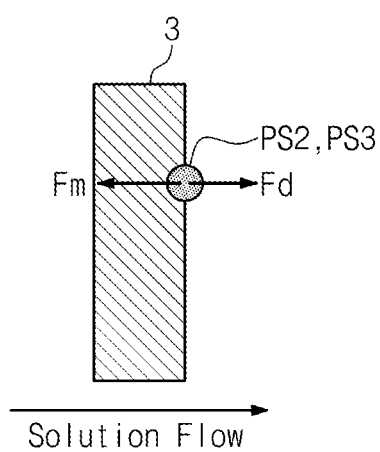
FIG. 4 illustrates movement of particles of material species in the multiple separation device illustrated in FIG. 3A.

FIG. 4 illustrates movement of particles of material species in the multiple separation device illustrated in FIG. 3A.

Referring to FIGS. 1 and 3A through 3C, a force applied to the material species PS1, PS2 and PS3 adjacent to the ferromagnetic pattern 3 is the sum of a magnetic force $F_m$ that the ferromagnetic pattern 3 pulls the material species PS1, PS2 and PS3 and a force $F_d$ caused by a flow of the compound solution in an opposite direction to the force $F_m$ Since as the number of magnetic nano-beads combined with the material species PS1, PS2 and PS3 increases, a magnetization quantity is large, the material species PS1, PS2 and PS3 are well taken to the ferromagnetic pattern 3. For instance, since a magnetic force $F_m$ applied to the third material species PS3 having the largest magnetization quantity may be greater than a force $F_d$ caused by a flow of the compound solution, the probability that the third material species PS3 is captured by the ferromagnetic patterns 3 adjacent to the inlet 1 becomes great. However, since a flow velocity is relatively high at this location, the first and second material species SP1 and SP2 having a magnetization quantity smaller than that of the third material species SP3 are more greatly affected by a force $F_a$ caused by a flow of the compound solution as compared with the magnetic force $F_m$ and thereby the first and second material species SP1 and SP2 float down the channel 2. While the first and second material species SP1 and SP2 float down the channel 2, the second material species SP2 may be captured by the ferromagnetic pattern 3 at a location where a flow velocity is relatively weak. The first material species SP1 having the smallest magnetization quantity may be captured by the ferromagnetic pattern 3 adjacent to the outlet 4 or may be discharged through the outlet 4. Thus, the cancer cell can be separated into cancer types depending on the number of magnetic nano-beads.

Referring to FIG. 1, cancer cells are analyzed/distinguished according to a capturing location of the ferromagnetic pattern 3 (S40). After all the blood samples to be tested flow down, remaining bloods in the channel 2 are removed using a buffer solution such as a saline solution. The captured cancer cells have to be prevented from breaking away from the ferromagnetic pattern 3 or being damaged by making a flow velocity of the buffer solution equal to or lower than that of the blood.

After removing the remaining bloods, estimation of whether a cancer cell exists and the type of cancer cell is possible through information about the number of captured cancer cells and locations where the cancer cells are captured obtained by performing an image analysis on a chip in which a cancer cell is captured. Since the locations where the cancer cells are captured are limited to the vicinity of the ferromagnetic pattern3, when performing an image analysis, it is sufficient to analyze a narrow area around the ferromagnetic pattern 3.

When it is additionally needed to analyze DNA using the captured cancer cells, the captured cancer cells have to be separated from the ferromagnetic pattern 3 and then collected. To collect the captured cancer cells after they are separated, the ferromagnetic pattern 3 has to be demagnetized. To achieve this, it is possible to demagnetize the ferromagnetic pattern 3 by applying a weak magnetic field of a direction opposite to a direction that demagnetizes the ferromagnetic pattern 3. The demagnetization of the ferromagnetic pattern 3 can be performed by removing the permanent magnet 7 used when capturing cancer cells and disposing a magnet having a weak strength of the opposite direction. A magnetic field applied to the ferromagnetic pattern 3 by the magnet having a weak strength has to have a strength corresponding to a coercive field of magnetic material constituting the ferromagnetic pattern 3. In the case that it is difficult to precisely control an applied magnetic field using a permanent magnet when the ferromagnetic pattern 3 is demagnetized, an electromagnet may be used. After the permanent magnet is removed and then an electromagnet is disposed at the same location to have a magnetic field of the opposite direction, a separation of the captured cancer cells can be checked by increasing a magnetic field gradually applied by controlling the amount of currents flowing through the electromagnet while supplying a buffer solution such as a saline solution. A magnetic field strength of when the captured cancer cells break away from the ferromagnetic pattern 3 is the strength close to the coercive field of the ferromagnetic pattern 3 and it is desirable to break the cancer cells away from the ferromagnetic pattern 3 at that strength. Since when an excessive large magnetic field is applied, the ferromagnetic pattern 3 is demagnetized in the opposite direction to pull the cancer cells that broke away from the ferromagnetic pattern 3 again, a magnetic field being applied when the cancer cells break away from the ferromagnetic pattern 3 has to be maintained around the coercive field of the ferromagnetic pattern 3. Since the coercive field of the ferromagnetic pattern 3 is different depending on a ferromagnetic material being used, it has to meet a ferromagnetic material being used.

Second Embodiment

FIG. 5A is a top plan view illustrating a multiple separation device in accordance with second embodiment of the inventive concept. FIG. 5B is a cross sectional view taken along the line A-A' of FIG. 5A.

Referring to FIGS. 5A and 5B, in a multiple separation device 101 in accordance with second embodiment, a plane shape of the channel 2 has a winding concave-convex structure and a width (W1, Wn) of the channel 2 is discontinuously and gradationally widened. The ferromagnetic pattern 3 may have a plurality of line shapes extending in a first direction X while crossing the channel 2. Depending on locations, a bottom surface of the channel 2 may be flat and a thickness of the channel 2 may be uniform. Since the width (W1, Wn) of the channel 2 increases, a flow velocity (v1, vn) of compound solution flowing through the channel 2 becomes slow as approaching the outlet 4 from the inlet 1. In the present embodiment, many ferromagnetic patterns 3 are disposed in the same flow velocity section to increase reliability of operation. By the principle described above, cancer cells can be separated into cancer types depending on the number of magnetic nano-beads.

Third Embodiment

FIG. 6A is a top plan view illustrating a multiple separation device in accordance with third embodiment of the inventive concept. FIG. 6B is a cross sectional view taken along the line A-A' of FIG. 6A.

Referring to FIGS. 6A and 6B, in a multiple separation device 102 in accordance with third embodiment, a width (W1, Wn) and a thickness of the channel 2 may be uniform at all locations of the channel 2. The channel 2 may be inclined. Top surfaces of the ferromagnetic patterns 3 are coplanar with top surfaces of the substrate 6 and are horizontal. Thus, a distance between the ferromagnetic patterns 3 and a bottom surface of the channel 2 may become gradually small as approaching the outlet 4 from the inlet 1. Even though the channel 2 is inclined, since the amount of compound solutions flowing through the channel 2 is very small, the compound solution is not affected by gravity. Thus, since a width and a thickness of the channel 2 is uniform, a flow velocity of the compound solution flowing through the channel 2 may be almost uniform at all locations of the channel 2. However, a capturing force (or magnetic force $F_n$, of FIG. 4) of the ferromagnetic pattern 3 which has an effect on the compound solution of the channel 2 may become great as approaching the outlet 4 from the inlet 1. Thus, as described with reference to FIG. 4, the first and second material species PS1 and PS2 having a magnetization quantity smaller than that of the first material species SP 1 are more affected by a force $F_d$ caused by a flow of the compound solution than the magnetic force $F_m$ and thereby the first and second material species PS1 and PS2 float down the channel 2. While the first and second material species SP1 and SP2 float down the channel 2, the second material species SP2 may be captured by the ferromagnetic pattern 3 at a location where the magnetic force $F_m$ is relatively strong. The first material species SP1 having the smallest magnetization quantity may be captured by the ferromagnetic pattern 3 adjacent to the outlet 4 or may be discharged through the outlet 4. Thus, the cancer cell can be separated into cancer types depending on the number of magnetic nano-beads.

Figure 7:
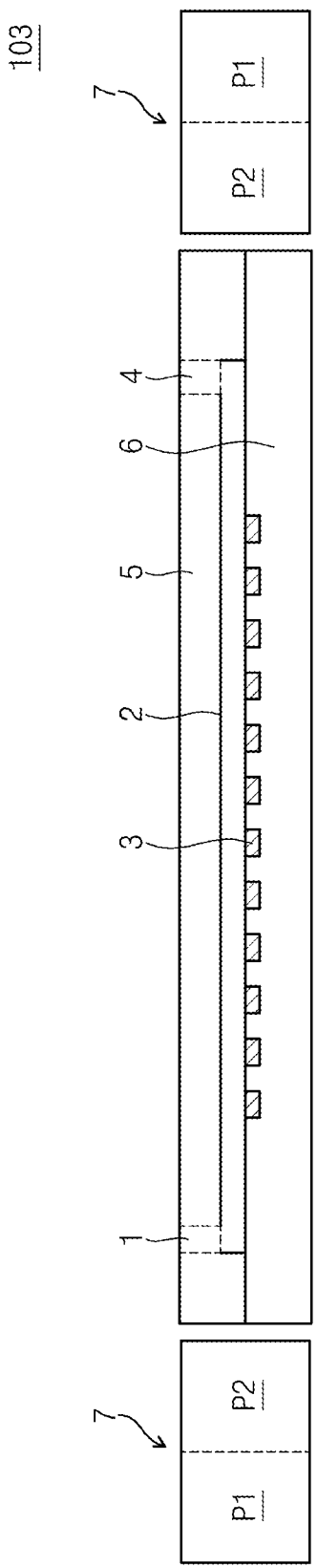

FIGS. 7 and 8 are cross sectional views of a multiple separation device in accordance with further embodiments of the inventive concept.

Referring to FIG. 7, in a multiple separation device 103 in accordance with the present embodiment, two permanent magnets 7 may be disposed on both sides of the channel 2. Referring to FIG. 8, in a multiple separation device 104 in accordance with the present embodiment, two permanent magnets 7 may be disposed under both sides of the channel 2. As illustrated in FIGS. 3B, 5B, 6B and 8, in the case that the permanent magnet 7 is located under the channel 2, since a magnetic force becomes weak as distance from a bottom surface of the channel 2 increases, the second and third material species PS2 and PS3 move around the bottom surface of the channel 2 and thereby the second and third material species PS2 and PS3 can be well captured in the channel 2 without deviation according to a channel height. The permanent magnet 7 may be variously disposed. Also, combinations of the embodiments of the inventive concept are possible.

The multiple separation device and the method of separating a blood cancer cell in accordance with some embodiments of the inventive concept can simply diagnose whether a cancer develops and distinguish cancer type. In addition, since they can completely remove interference effect of blood cells, they can greatly improve specificity as compared with existing technologies.

The embodiments described above are not realized only through a device and a method, but an expert of technical field which belongs to the present inventive concept can easily realize the embodiments.

What is claimed is:

1. A method of separating a blood cancer cell comprising:
producing a compound solution including cancer cells with which a magnetic nano-bead is combined by mixing the magnetic nano-bead with which an antibody specifically reacting to a cancer cell is combined with blood to be tested;
injecting the compound solution into a channel in which ferromagnetic patterns are disposed on a bottom surface of the channel; and
capturing cancer cells in the channel depending on the type of the cancer cells by varying an amount of magnetic force applied to the compound solution according to a location of the channel.

2. The method of claim 1, further comprising: distinguishing cancer cells according to a capturing location of the ferromagnetic pattern.

3. The method of claim 2, wherein distinguishing cancer cells according to a capturing location of the ferromagnetic pattern comprises:
removing the compound solution which remains in the channel;
separating the cancer cells from a surface of the ferromagnetic pattern; and
analyzing DNA of the cancer cells.

4. The method of claim 3, wherein separating the cancer cells from a surface of the ferromagnetic pattern comprises demagnetizing the ferromagnetic pattern by applying a magnetic field in an opposite direction of a magnetic field magnetizing the ferromagnetic pattern.

5. The method of claim 4, wherein the magnetic field has a strength corresponding to a coercive field of the ferromagnetic pattern.

6. The method of claim 4, wherein demagnetizing the ferromagnetic pattern is performed using a permanent magnet or an electromagnet.

7. The method of claim 1, wherein an amount of magnetic force at a first end of the channel is less than an amount of magnetic force at a second end of the channel, and the amount of magnetic force in the channel varies progressively from the first end of the channel to the second end of the channel.

8. The method of claim 1, further comprising varying a velocity of the compound solution according to a location of the channel,
wherein the velocity is varied by gradually changing a volume of the channel.

* * * * *